United States Patent
Levy et al.

(10) Patent No.: US 9,433,800 B2
(45) Date of Patent: **\*Sep. 6, 2016**

(54) ACTIVATABLE PARTICLES, PREPARATION AND USES

(71) Applicant: NANOBIOTIX, Paris (FR)

(72) Inventors: Laurent Levy, Paris (FR);
Jean-Francois Hochepied, Paris (FR);
Jeremy Balencie, Veneux-les-Sablons (FR); Paras Nath Prasad, Williamsville, NY (US); Earl Jim Bergey, South Dayton, NY (US);
Edouard Andre Panak, Toulouse (FR);
Abdel Kader Boussaha, Paris (FR)

(73) Assignee: NANOBIOTIX, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/707,529

(22) Filed: May 8, 2015

(65) Prior Publication Data
US 2015/0238775 A1      Aug. 27, 2015

Related U.S. Application Data

(62) Division of application No. 11/579,867, filed as application No. PCT/FR2005/001145 on May 9, 2005.

(30) Foreign Application Priority Data

May 10, 2004 (FR) ..................... 04 05036

(51) Int. Cl.
| | |
|---|---|
| *A61N 5/06* | (2006.01) |
| *A61K 41/00* | (2006.01) |
| *A61K 49/04* | (2006.01) |
| *B82Y 5/00* | (2011.01) |
| *A61N 5/10* | (2006.01) |
| *C12N 13/00* | (2006.01) |

(52) U.S. Cl.
CPC ........... *A61N 5/062* (2013.01); *A61K 41/0038* (2013.01); *A61K 41/0052* (2013.01); *A61K 49/0423* (2013.01); *A61N 5/10* (2013.01); *B82Y 5/00* (2013.01); *C12N 13/00* (2013.01); *A61N 2005/0661* (2013.01); *A61N 2005/1098* (2013.01)

(58) Field of Classification Search
CPC ..................... A61K 41/0038; A61K 49/0423; A61K 41/0052; B82Y 5/00; C12N 13/00; A61N 5/062; A61N 2005/0661; A61N 2005/1098; A61N 5/10
See application file for complete search history.

(56) References Cited

U.S. PATENT DOCUMENTS

| | | |
|---|---|---|
| 5,985,173 A | 11/1999 | Gray et al. |
| 2002/0127224 A1 | 9/2002 | Chen |
| 2004/0014060 A1 | 1/2004 | Hoheisel et al. |
| 2007/0217996 A1 | 9/2007 | Levy et al. |
| 2007/0218049 A1 | 9/2007 | Chen et al. |
| 2007/0269382 A1 | 11/2007 | Santra et al. |

FOREIGN PATENT DOCUMENTS

EP    1 162 626 A1    12/2001

OTHER PUBLICATIONS

Jacobsohn et al, "Luminescent properties of nanophosphors", Radiation Measurements 42 (2007) 675-678.
International Search Report of PCT/FR2005/001145, mailed Oct. 18, 2005.
Hitoshi et al., "Hydroxyl radical generation depending on O2 or H20 by a photocatalyzed reaction in an aqueous suspension of titanium dioxide", Bioscience Biotechnology and Biochemistry, vol. 62, No. 12, Dec. 1998, pp. 2306-2311, XP009042440.
Hu et al, "Soft x-ray excited optical Luminescence: Some recent applications", Rev. Sci. Instruments. 2002, 73(3), p. 1379-81.
Fujii et al, "Synthesis of $TiO_2$/CdS nanocomposite via $TiO_2$ coating on CdS nanoparticles by compartmentalized hydrolysis of Ti alkoxide", J. Mat. Sci., 2001, 36(2), p. 527-532.
Wang et al, "Nanomaterials and singlet oxygen photosensitizers: potential applications in photodynamic therapy", J. Mat. Chem., 2004, 14, p. 487-493.

*Primary Examiner* — Michael G Hartley
*Assistant Examiner* — Leah Schlientz
(74) *Attorney, Agent, or Firm* — Nixon & Vanderhye P.C.

(57) ABSTRACT

The present invention relates to novel activatable particles which can be used in the health sector. The invention more particularly relates to composite particles which can generate free radicals or heat when excited by X rays, and to the uses thereof in health, particularly human. The inventive particles comprise an inorganic-based, and optionally organic-based, nucleus and can be activated in vivo, in order to label or alter cells, tissues or organs. The invention also relates to methods for the production of said particles, and to pharmaceutical or diagnostic compositions containing same.

3 Claims, 5 Drawing Sheets

1 …

ACTIVATABLE PARTICLES, PREPARATION AND USES

This application is a divisional of U.S. application Ser. No. 11/579,867 (issued as U.S. Pat. No. 9,162,079 on Oct. 20, 2015), filed Nov. 8, 2006 (published as US 2007-0217996 A1), which is a U.S. National Phase of International Application No. PCT/FR2005/001145, filed May 9, 2005, which designated the U.S. and claims priority of FR 0405036, filed 10 May 2004, the entire contents of each of which are hereby incorporated by reference.

The present application relates to novel activatable particles which can be used in the health sector. It more particularly relates to composite particles which can generate free radicals or heat when excited by X rays, and to the uses thereof in health, particularly human. The inventive particles comprise an inorganic-based, and optionally organic-based, nucleus and can be activated in vivo, by controllable external excitation, in order to label or alter cells, tissues or organs. The invention also relates to methods for the production of said particles, and to pharmaceutical or diagnostic compositions containing same.

Photodynamic therapy (PDT) has been described and is currently used to treat superficial cancers such as those of the skin or oesophagus (see for example McCaughan, J. S. Jr., Drugs and Aging. 15: 49-68 (1999) "*Photodynamic Therapy: A Review*"). Said treatment is based on the production of free radicals by photosensitive molecules, during exposure to strong UV rays or laser. In fact, the activated molecules convert the surrounding oxygen to free radicals which are highly reactive species producing irreversible damage in cells. The main cellular organelles attacked are the mitochondria, cell and nuclear membranes, lysosomes, etc.

The photosensitive molecules are injected by the intravenous route and generally accumulate at higher concentration in tumor tissue. This makes it possible, after a given time, to have a higher concentration in the tissues to be treated than in healthy tissues. When said molecules are exposed to light (having a suitable wavelength), they produce free radicals from oxygen, which then react with vital components of the cell.

Photodynamic therapy nonetheless has some limitations. For instance, patients may develop light sensitivity, which restricts the number of administrations of said therapy in a given individual. Furthermore, the low wavelengths of the rays used to excite the photosensitive molecules preclude passage through a large thickness of tissue, which has the advantage of low toxicity towards other tissues, but restricts the indication to superficial cancers (skin and subcutaneous). Other potential problems inherent to the use of photodynamic therapy are linked to the toxicity of the photosensitive molecules and the need, in some cases, to use oxygen to "load" the tissues to be treated.

Another approach using $TiO_2$ particles has shown that it was possible to generate free radicals from water and oxygen molecules under excitation by UV [Shibata et al., Bioscience Biotechnology and Biochemistry 62: 2306-2311 (1998)]. This approach has been used in in vitro and in vivo models of bladder cancer.

A further approach, based on the use of particles that can be activated by applying a magnetic field, is described in U.S. Pat. No. 6,514,481. The present invention describes a novel class of particles, named NanoXRay, which can be used in photodynamic therapy. In particular, the present invention notably describes novel particles, activatable by X rays and/or by UV rays, which can induce a therapeutic or diagnostic response in vivo, in a targeted manner, even in deep tissues.

Hence the present invention discloses novel compounds which can be used in therapy and/or diagnostics (for example in imaging), particularly in humans. The inventive particles can be employed to label, alter or destroy cells, tissues or organs, if necessary in a targeted manner, in combination with a source of X rays and/or UV rays. The inventive particles can be used in any type of tissue, superficial or deep, in any mammalian organism.

A first aspect of the invention therefore relates to composite particles or nanoparticle aggregates, which can generate free radicals and/or heat when excited by X rays and/or UV rays.

According to another aspect, the invention relates to any particle or any nanoparticle aggregate composed of at least two inorganic compounds (of different compositions), which can be surface treated so as to specifically target biological tissues or cells, and whose action is to disturb or alter a biological tissue and/or a cell under the effect of a source of excitation.

A more particular object of the invention is based on a biocompatible composite particle or nanoparticle aggregate (which can generate free radicals or heat when excited by X rays), comprising:
 a nucleus comprising a first inorganic compound absorbing X rays and emitting UV-visible energy, and a second compound, inorganic or organic, absorbing UV-visible energy and producing free radicals on contact with water or oxygen, and
 optionally, a biocompatible coating.

Another object of the invention relates to a method of preparation of particles or aggregates such as defined hereinabove.

Another object of the invention is based on pharmaceutical or diagnostic compositions, comprising particles or aggregates such as defined hereinabove or which can be obtained by the aforementioned method.

A further object of the invention is based on the use of compositions, particles or aggregates such as defined hereinabove, in order to label or destroy cells, tissues or organs, in vitro, ex vivo or in vivo, and the corresponding methods.

In the spirit of the invention, the term composite "particle" or "nanoparticle aggregate" refers to complex, synthetic products, of small size. The shape thereof can vary, for example round, flat, elongated, spherical, oval, and the like. The shape can be determined or controlled by the method of production, and adapted by the person of the art according to the desired applications.

The shape of the particles does not have a major influence on the properties thereof, in particular on the yield of free radical formation. However, the shape can influence the "biocompatibility" of the particles. Thus, for pharmacokinetic reasons, particles or nanoparticle aggregates having an essentially spherical or round shape are preferred. Also, particles or nanoparticle aggregates having a quite homogeneous shape are preferred.

In a preferred manner, the size of the particles or nanoparticle aggregates according to the invention is typically comprised between approximately 4 and 250 nm. For in vivo applications in humans or animals, particles or nanoparticle aggregates having a size comprised between 4 and 100 nm, even more preferably between 4 and 50 nm, are more particularly preferred. In fact, the size of the objects must ideally be small enough to enable them to diffuse in the body (tissues, cells, blood vessels, etc.), essentially without being captured by macrophages (phagocytosis) and without causing significant obstruction. Advantageously, such effects can be obtained in humans with particles having a size less than 100 nm, preferably less than 50 nm.

The particles or aggregates according to the invention must be biocompatible, that is to say, they must be able to be administered to an organism, typically a mammal. Said biocompatibility can be ensured for example by the nature of the compounds constituting the particle and/or by the optional coating.

As indicated earlier, the inventive particles comprise at least two types of inorganic compounds having particular properties, optionally covered with a coating.

The first compound forming the nucleus of the particle is an inorganic compound (or a mixture of compounds) absorbing X rays and emitting UV-visible energy. The main function of said material is to absorb X rays and to generate UV-visible energy, in particular UV rays. Advantageously, an inorganic compound is used in the form of oxide, hydroxide, oxysulfide or salt, preferably doped with a doping agent, preferably selected from among the rare earth elements. The properties of said first compound can be adjusted by the person of the art according to the type of doping used, the electronic configuration and the crystal environment surrounding said doping agent, and the concentration thereof. In a particularly preferred manner, the doping agent is selected from among the rare earth elements, preferably at a cation concentration (doping agent) less than or equal to approximately 15% in solid solution. Said percentage corresponds to the ratio of the rare earth cations to the cations of the inorganic compound.

In a particular embodiment, the invention relates to a particle or nanoparticle aggregate such as defined hereinabove, wherein the first inorganic compound is selected from among oxides and hydroxides doped with a rare earth element, preferably at a concentration less than 15% in solid solution, and mixed compounds of Ge, Hf and/or Zr oxides, doped or not, preferably doped with the aid of rare earth cations.

The first inorganic compound (or principal compound) can advantageously be selected in the group consisting of the following compounds: $Y_2O_3$, $(Y,Gd)_2O_3$, $CaWO_4$, $GdO_2S$, $LaOBr$, $YTaO_3$, $BaFCl$, $Gd_2O_2S$, $Gd_3Ga_5O_{12}$, $Rb_3Lu(PO_4)_2$, $HfGeO_4$, and $Cs_3Lu(PO_4)_2$. Particularly preferred compounds in the scope of the invention are the oxides $Y_2O_3$ and $HfGeO_4$.

Advantageously, the doping agent which is used is a rare earth element selected in the group consisting of Gd, Eu, Tb, Er, Nb, Pr and Ce. Gd, Eu and Tb are particularly preferred doping agents.

In a specific example of inventive particle, the first inorganic compound is selected from among $Y_2O_3$ doped with Gd, Eu or Tb.

In a second specific example of inventive particle, the first inorganic compound is $HfGeO_4$ doped or not, preferably doped, or $HfGeO_4$ in mixed solution with Zr (which can comprise up to 50% of the mixed solution).

It is understood that other inorganic compounds, oxides, hydroxides, oxysulfides or salts and doping agents can be envisioned by the person of the art to produce the inventive particles. In addition, several oxides, hydroxides, oxysulfides or salts and/or doping agents can be used as a mixture in a same inventive particle.

The second compound forming the nucleus of the particle is an inorganic or organic compound (or a mixture of compounds) absorbing UV-visible energy and producing free radicals on contact with water or oxygen. The main function of said material is to absorb UV-visible energy, particularly UV rays, and to convert the water (or $O_2$) present at the surface of said compound into free radicals by a reaction of the photocatalytic type.

Advantageously, the second compound is an inorganic compound, which can be selected from among semiconductor compounds, such as in particular $TiO_2$, ZnO and, in a non-restrictive manner, CdS, CdSe, CdTe, MnTe and mixed solutions (for example CdZnSe, CdMnSe, etc.), optionally doped (as described for the first inorganic compound).

In a particular embodiment, $TiO_2$ is used as second inorganic compound, advantageously in anatase form, and optionally doped.

In another variant embodiment, the second compound can be an organic molecule absorbing in the UV region and generating free radicals in the presence of oxygen (for example certain molecules used in photodynamic therapy). However, it is preferable to use an inorganic compound as second compound.

Within the nucleus of the inventive particles, the inorganic (and optionally organic) compounds can be arranged or organized in different ways.

For instance, in a first variant embodiment, the first inorganic compound forms the core of the nucleus, and the second compound (inorganic or organic) is in the form of a layer or nanoparticles at the surface of the core (see FIGS. 1A and 1B).

In a specific variant embodiment, the two inorganic compounds of the nucleus are arranged in multiple successive layers, the first inorganic compound preferably forming the internal layer (core).

Thus, a preferred embodiment of the invention consists of particles whose nucleus comprises a core composed of the first inorganic compound, surrounded by a layer formed by the second compound (FIG. 1A). The core of the nucleus formed by the first inorganic compound typically has a size comprised between approximately 5 and 50 nm, for example between 7 and 40 nm, and/or the layer formed by the second compound at the surface of the core has a thickness typically comprised between approximately 1 and 30 nm, for example between 2 and 25 nm.

In another variant embodiment, the two compounds of the nucleus are present in the form of a mixture of nanoparticles (FIG. 1C). Said nanoparticles can have various sizes and shapes. Generally, as a guide, the nanoparticles have a size comprised between approximately 3 and 100 nm and preferably between 5 and 25 nm.

In a further variant embodiment, the two inorganic compounds of the nucleus are present in the form of two nuclei in contact with each other (FIG. 1D).

Generally, the efficacy or the properties of the particles can be adapted by the person of the art by changing the relative amount of the two types of compounds, the overlap between the emission and absorption spectra of the two inorganic compounds, the crystal structure of the materials, the area of contact between the second compound and water and/or the distance between the first and second compounds.

In regard to the relative amount of the two compounds, particles in which the two compounds are present in similar amounts are typically preferred. Nonetheless, the ratio of the amount or the concentration of the first compound to the second compound can be adjusted by the person of the art, preferably within a range of 0.1 to 10, more preferably from 0.2 to 5.

Moreover, the experiments conducted by the inventors show that the greater the overlap between the emission spectrum of the first inorganic compound (forming the core) and the absorption spectrum of the second compound, the higher the yield of particles.

Similarly, the larger the area of contact between the second compound (for example $TiO_2$) and water, the higher the yield.

Furthermore, the energy transfer yield in the particles also depends on the distance between the first inorganic compound (forming the core) and the second. The shorter this distance and/or the greater the area of contact, the more effective the energy transfer and the more active the particle.

The person of the art can therefore adjust the properties of the particles by varying the aforementioned parameters, for example according to the planned uses (diagnostic, therapeutic, etc.).

It is understood that, in addition to the two types of compounds described hereinabove, the inventive particles can comprise other molecules, compounds or structure or surface materials, intended to improve their stability, property, function, specificity, etc.

Thus, as indicated earlier, the particles or nanoparticle aggregates according to the invention can additionally comprise a surface component allowing to specifically target biological tissues or cells. Said surface component can be bound to the particles by any means, preferably covalent, optionally via a linker. It can be associated with one of the inorganic compounds or with any coating which is present, as described hereinbelow.

The surface targeting component can be any biological or chemical structure displaying an affinity for molecules present in the human or animal body. For instance, it can be a peptide, polypeptide, nucleotide, polynucleotide, hormone, vitamin, and the like, and, in general, any ligand of molecules (for example receptors, markers, antigens, etc.). Ligands of molecules expressed by pathological cells, in particular ligands of tumor antigens, hormone receptors, cytokine receptors or growth factor receptors, for example, can be mentioned by way of illustration.

The targeting component, when present, makes it possible to preferentially direct the inventive particles towards the cells, tissues or organs of interest, and thereby confine the action to these tissues. Said targeting is especially useful when the particles are administered by the systemic route, for example for deep tissues.

As indicated earlier, the particles or nanoparticle aggregates according to the invention can additionally comprise a coating. Advantageously, said coating preserves the integrity of the particles in vivo, ensures or improves the biocompatibility thereof, and facilitates the functionalization thereof (for example with spacer molecules, biocompatible polymers, targeting agents, proteins, etc.).

The coating can be composed of any amorphous or crystalline structure. In order to preserve the activity of the inventive particles, it is desirable that the coating allow the diffusion of small molecules and free radicals. In particular, it is important that the coating allow the passage of water (or $O_2$) and the radical form thereof after transformation. This can be accomplished by using materials which are porous and/or a coating layer which has low thickness and is porous. Thus for example, typically a coating is employed which has a porosity comprised between 0.2 and 10 nm. In addition, the coating has a thickness generally comprised between approximately 0.1 and 50 nm, for example between 0.2 and 40 nm.

In general, the coating can be non-biodegradable or biodegradable. Examples of non-biodegradable coatings are one or more materials selected in the group consisting of silica, agarose, alumina, a saturated carbon polymer or an inorganic polymer, reticulated or not, modified or not (polystyrene for example). Examples of biodegradable coatings are for example one or more materials selected in the group consisting of biological molecules modified or not, natural or not, a biological molecular polymer modified or not, of natural shape or not, or a biological polymer, such as a saccharide, oligosaccharide, polysaccharide, polysulfated or not, for example dextran. The aforementioned materials or compounds can be used alone or in mixtures or assemblies, composite or not, covalent or not, optionally in combination with other compounds. Moreover, it is also possible to use any aforementioned material, naturally or artificially water- or lipid-soluble.

The coating preferably comprises one or more compounds selected in the group consisting of silica ($SiO_2$), alumina, polyethylene glycol (PEG) or dextran, optionally in mixture (s).

The coating can also contain different functional groups (or linker segments), allowing any molecule of interest to bind to the surface of the particle.

Examples of useful functional groups are $(CH_2)_n COOH$, in which n is an integer number from 1 to 10.

For example, the molecules coupled to the surface of the particle can be:
the targeting agent;
a molecule ensuring or improving biocompatibility; or
a molecule enabling the particle to escape the immune system (and in particular to avoid interactions with macrophages and SRE).

In a preferred embodiment, the particles or nanoparticle aggregates according to the invention comprise a coating to which the surface targeting component is bound, preferably by means of a linker.

Preferred particles or aggregates of the invention comprise, as first inorganic compound, $Y_2O_3$ doped with a rare earth element or $HfGeO_4$ optionally doped and/or in mixed solution with Zr; as second inorganic component, $TiO_2$ and, preferably, a $SiO_2$ or dextran-based coating.

In the spirit of the invention, particular particles or aggregates comprise, as first inorganic compound, $Y_2O_3$:Gd; as second inorganic compound, anatase $TiO_2$ and, preferably, a $SiO_2$ coating.

Other particular particles or aggregates in the context of the invention comprise, as first inorganic compound, $Y_2O_3$:Tb; as second inorganic compound, anatase $TiO_2$ and, preferably, a dextran-based coating.

Particular examples of particles are:
A particle or an aggregate comprising a core comprising $Y_2O_3$:Gd covered with a layer of $TiO_2$, and a $SiO_2$ coating, preferably functionalized. Preferably, the core is round or spherical in shape, with a size comprised between approximately 5 and 50 nm (typically about 30 nm), the $TiO_2$ layer has a thickness comprised between approximately 5 and 30 nm (typically about 5 nm), and the coating has a thickness comprised between approximately 1 and 50 nm (typically about 5 nm).
A particle or a nanoparticle aggregate comprising a nucleus comprising microparticles of $Y_2O_3$:Tb and of $TiO_2$, and a dextran-based coating, preferably functionalized.
A particle or an aggregate comprising a core comprising $HfGeO_4$ covered with a layer of $TiO_2$, and a $SiO_2$ coating, preferably functionalized.

Another object of the invention relates to a method of production of particles or nanoparticle aggregates such as defined hereinabove, comprising:

mixing the two compounds such as defined hereinabove in order to form a particle or an aggregate and, optionally coating the particle or aggregate.

In a variant embodiment, the method additionally comprises a functionalization step, comprising adding a targeting component on the particle or aggregate.

The materials which compose the particles or aggregates according to the invention can be produced by different techniques, known to those skilled in the art. The method can be adapted by the person of the art according to the nature of the compounds employed, and according to the arrangement thereof in the particles and aggregates. For instance, in a particular embodiment, the method comprises:

preparing the particle core comprising the first inorganic compound, covering the core thus formed with a layer comprising the second compound, and, preferably, coating the particle or aggregate thus obtained with a porous material.

Alternative methods for producing materials which can be used for the production of the inventive particles are described for example in Nelson et al., Chem. Mater. 2003, 15, 688-693 "Nanocrystalline Y2O3:Eu Phosphors Prepared by Alkalide Reduction" or else in Liu et al., Journal of Magnetism and Magnetic Materials 270 (2004) 1-6 "Preparation and characterization of amino-silane modified superparamagnetic silica nanospheres".

In a specific embodiment, described in detail in the experimental section, enabling the production or synthesis of a particle or aggregate comprising a core comprising $Y_2O_3$:Eu covered with a layer of $TiO_2$ and a $SiO_2$ coating, the method comprises the following steps:

the $Y_2O_3$:Eu nanoparticles are produced via a reduction with $YCl_3$, $EuCl_3$ and crown ether in homogeneous medium, the $TiO_2$ layer can be added by precipitating $TiCl_4$ in acidic solution, then, the optional silica layer is obtained by precipitating sodium silicate in basic medium.

In a second specific embodiment, described in detail in the experimental section, enabling the production or synthesis of a particle or aggregate comprising a core comprising $HfGeO_4$ covered with a layer of $TiO_2$ and a $SiO_2$ coating, the method comprises the following steps:

synthesizing the core by co-precipitation of hafnium and amorphous germanium salts, covering with $TiO_2$, and coating with $SiO_2$ using TEOS and/or sodium silicate.

Another object of the invention is based on any composition comprising particles or aggregates such as defined hereinabove and/or which can be obtained by the method described hereinabove. While not mandatory, the particles in the inventive compositions advantageously have a quite homogeneous size and shape. Generally, the compositions comprise between 0.3 and 3000 mg of particles per 100 ml. The compositions can be in the form of a solid, liquid (particles in suspension), gel, paste, and the like.

A particular object of the invention relates to a pharmaceutical composition comprising particles or nanoparticle aggregates such as defined hereinabove and, optionally, a pharmaceutically acceptable excipient or vehicle.

Another particular object of the invention relates to a diagnostic or imaging composition comprising particles or nanoparticle aggregates such as defined hereinabove and, optionally, a physiologically acceptable excipient or vehicle.

The excipient or vehicle which is employed can be any classical support for this type of application, such as for example saline, isotonic, sterile, buffered solutions, and the like. They can also comprise stabilizers, sweeteners, surfactants, and the like. They can be formulated in ampoules, bottles, as tablets, capsules, by using known techniques of pharmaceutical formulation.

The compositions, particles and aggregates of the invention can be used in many fields, particularly in human or veterinary medicine. Under the effect of X rays, the nanoparticle core is excited and produces UV-visible energy, in particular UV. Said UV rays excite the second compound which, upon contact with water, generates free radicals. Depending on the duration of exposure to the source of excitation, the particles can thus enable the destruction of tissues (exposure time for example of several minutes, for example 5 minutes) or, simply, a visualization (imaging, diagnostics: very short exposure times of roughly a few seconds). Thanks to the high penetration of X rays, the inventive particles can be used to scan any tissue in the body. They can also be used with a source of UV excitation, for tissues on the surface or in body cavities (skin, bladder, lung, colon, etc.).

Hence a particular object of the invention is based on the use of compositions, particles or nanoparticle aggregates such as defined hereinabove, in combination with X rays, for producing a medicament intended to destroy target cells.

Another object of the invention is based on the use of compositions, particles or nanoparticle aggregates such as defined hereinabove, in combination with UV rays, for producing a medicament intended to destroy superficial or cavity target cells.

Another particular object of the invention is based on a method for inducing or causing the lysis or destruction of target cells, in vitro, ex vivo or in vivo, comprising contacting target cells with one or more particles or nanoparticle aggregates such as defined hereinabove, during a period of time sufficient to allow the particles or aggregates to penetrate inside the target cells and, exposing the cells to X rays or UV rays, said exposure inducing or causing the lysis or destruction of said target cells.

The target cells can be any pathological cells, that is to say, cells involved in a pathological mechanism, for example proliferative cells, such as tumor cells, stenosing cells (smooth muscle cells), or immune system cells (pathological cell clones). A preferred application is based on the treatment (for example the destruction or functional alteration) of cancer cells.

In this regard, a particular object of the invention is based on the use of compositions, particles or nanoparticle aggregates such as defined hereinabove (in combination with X rays or UV rays) for producing a medicament intended for the treatment of cancer.

Another particular object of the invention is based on a method for inducing or causing the lysis or destruction of cancer cells, in vitro, ex vivo or in vivo, comprising contacting cancer cells with one or more particles or nanoparticle aggregates such as defined hereinabove, during a period of time sufficient to allow the particles or aggregates to penetrate inside the cancer cells and, exposing the cells to X rays or UV rays, said exposure inducing or causing the lysis or destruction of said cells.

Another object of the invention relates to a method of cancer treatment, comprising administering to a patient suffering from a cancer a composition or particles or nanoparticle aggregates such as defined hereinabove, in conditions allowing the particles or nanoparticle aggregates to penetrate inside the cancer cells, and subsequently treating the patient in the presence of a source of excitation selected from among X rays and UV rays, leading to an alteration, disturbance or functional destruction of the patient's cancer cells, thereby treating the cancer.

The invention can be used to treat any type of cancer, in particular solid tumors, metastasized or not, for example selected in the group consisting of cancers of the lung, liver, kidney, bladder, breast, head and neck, brain, ovaries, prostate, skin, intestine, colon, etc.

The irradiation can be applied at any time after administration of the particles, on one or more occasions, by using any currently available system of radiotherapy or radiography. The particles can be administered by different routes, preferably by systemic or local injection, or orally. Repeated injections or administrations can be given, where necessary.

In general and in a non-restrictive manner, the following rays can be applied in different cases to excite the particles:
Superficial X rays (20 to 50 keV): to excite nanoparticles near the surface (penetration of a few millimeters).
Diagnostic X rays (50 to 150 keV).
X rays (ortho voltage) of 200 to 500 keV which can penetrate to a tissue thickness of 6 cm.
X rays (mega voltage) of 1000 keV to 25,000 keV. For example the excitation of nanoparticles for the treatment of prostate cancer can be carried out via five focused X rays with an energy of 15,000 keV.

In the field of diagnostics, the inventive particles can be used as contrast agent, for detecting and/or visualizing any type of tissue. Thus, an object of the invention is the use of compositions, particles or nanoparticle aggregates such as defined hereinabove, in combination with X rays, for producing a composition intended for the detection or the visualization of cells, tissues or organs.

Another object of the invention is based on the use of compositions, particles or nanoparticle aggregates such as defined hereinabove, in combination with UV rays, for producing a composition intended for the detection or the visualization of superficial or cavity cells, tissues or organs.

The term "in combination" indicates that the sought-after effect is obtained when the cells, tissues or organs of interest, having partially incorporated the nanoparticles of the invention, are excited by the defined source. However, it is not necessary for the particles and rays to be administered simultaneously, nor according to the same protocol.

The term "treatment" denotes any improvement in pathological signs, such as in particular a reduction in the size or growth of a tumor or a pathological area of tissue, the suppression or destruction of pathological cells or tissues, a slowing of disease progression, a reduction in the formation of metastases, a regression or a complete remission, etc.

The inventive particles can also be used in vitro or ex vivo.

Other aspects and advantages of the invention will become apparent in the following examples, which are given for purposes of illustration and not by way of limitation.

EXAMPLES

1. Production of $Y_2O_3$ Nanoparticles Doped with Erbium or Gadolinium $Y_2O_3$ nanoparticles doped with erbium or gadolinium were synthesized from functionalized surfactants (Y-AOT3, Eu-AOT3, and Gd-AOT3). A suitable surfactant mixture (based on the desired final concentration [Eu-AOT3]/[Y-AOT3]=0.01; 0.05; 0.1; 0.15) was dispersed in isooctane or cyclohexane. Water was added to promote micelle formation. Micelle size, which affects the size of the materials obtained, was controlled by the amount of water added to the mixture. The hydroxide was formed by base addition. The particles were then washed with a water/ethanol mixture, dried and heated at 800° C. so as to form crystalline nanoparticles.

Figure 1:
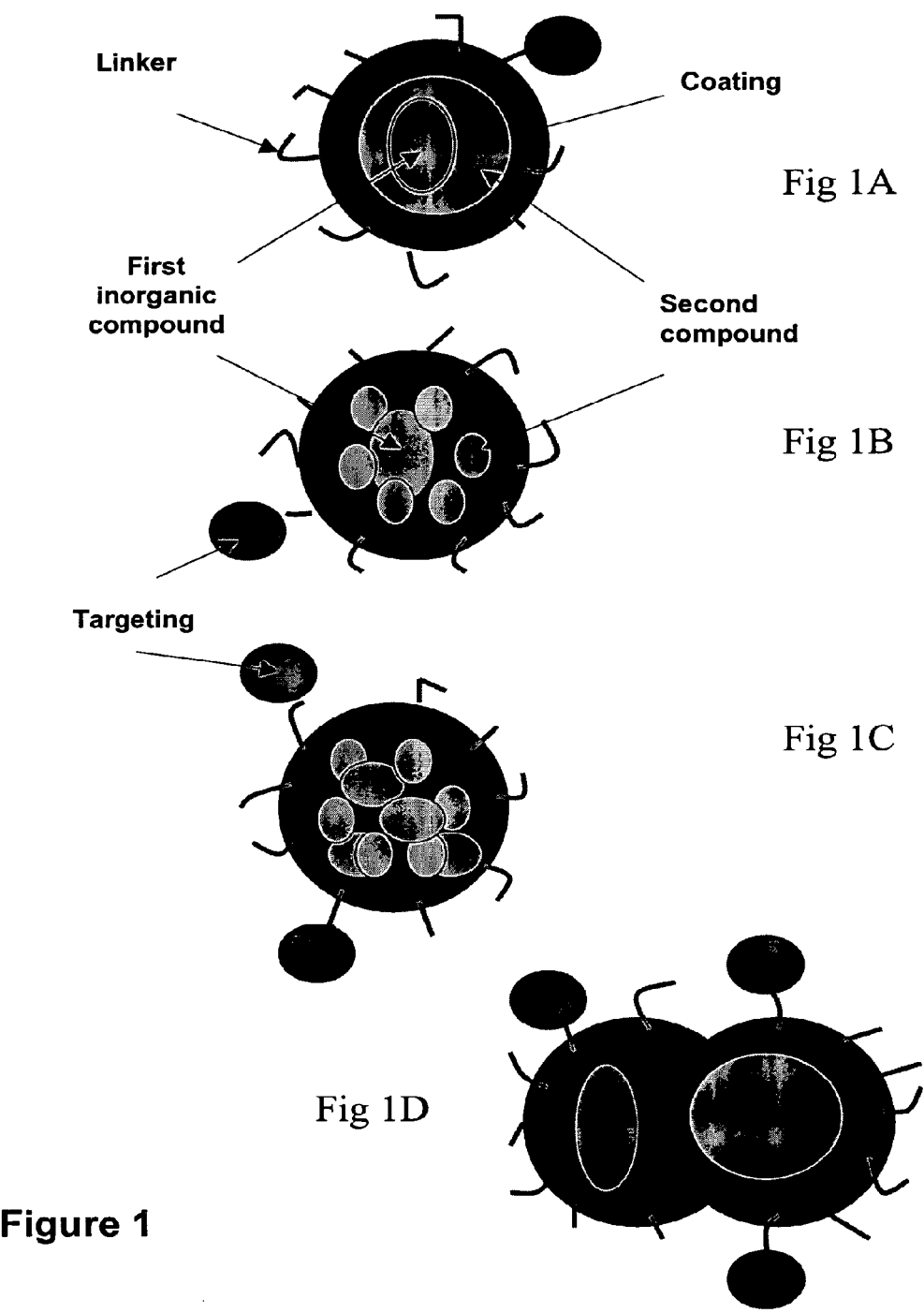
FIGS. 1A-1D provide an illustration of the inventive particles structure.
Figure 2:
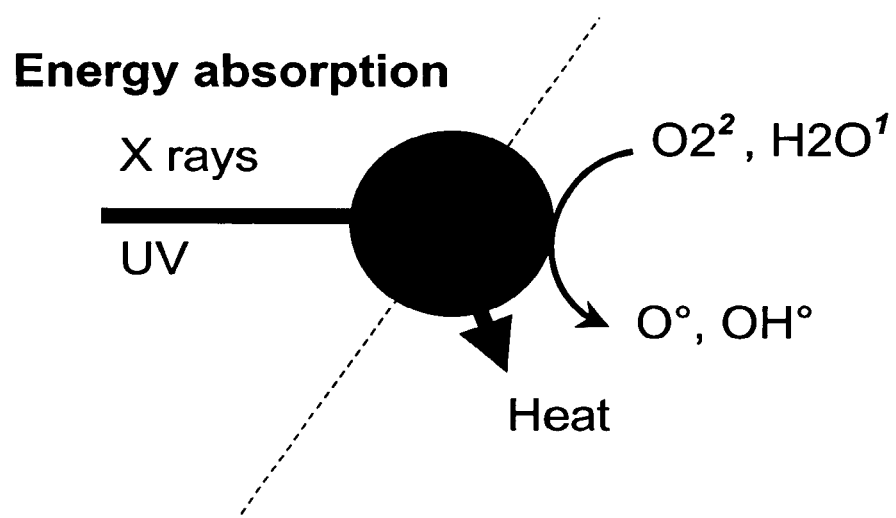
FIG. 2 depicts the mode of activation of the inventive particles in the presence of an Xray source.
Figure 3:
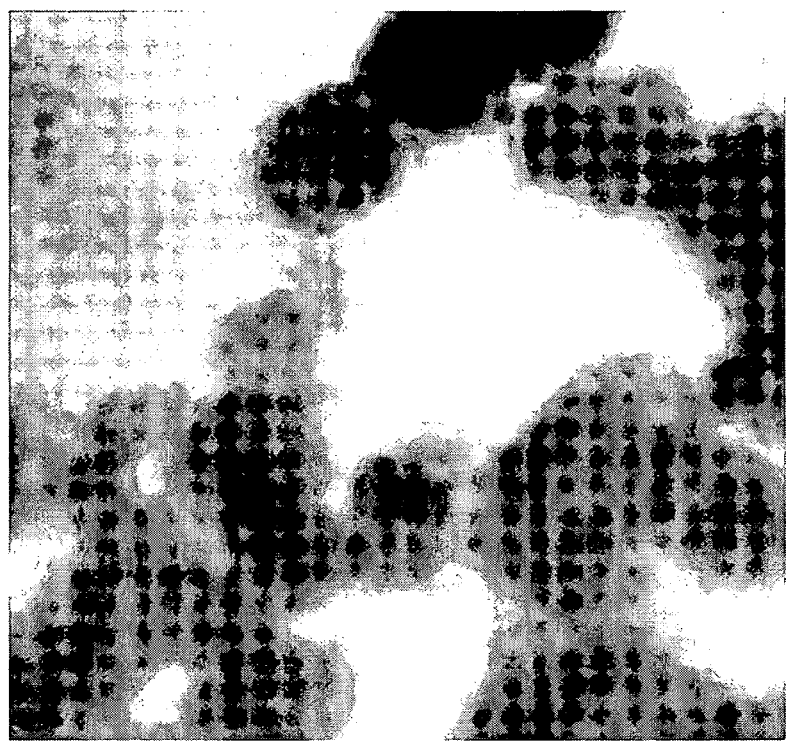
FIG. 3 is a transmission electron microscopy image showing gadolinium-doped $Y_2O_3$ nanoparticles.

10 mg of nanoparticles were dispersed in 50 ml of water at pH 7.5. A drop of this dispersion was deposited on a copper/carbon grid and observed under a transmission electronic microscope. A microscopic photograph is shown in FIG. 3.

The compounds so produced showed UV fluorescence when excited with X rays (for Gd-doped $Y_2O_3$).

2. Production of $HfGeO_4$ Nanoparticles Coated with Titanium Oxide and Silica

The core material, $HfGeO_4$, was synthesized by simple co-precipitation of hafnium ($HfOCl_2$, 8 $H_2O$) and amorphous germanium ($GeO_2$) salts in aqueous medium. A heat treatment comprised between 4 hours and 10 hours at 1100° C. or at a lower temperature then allowed the $HfGeO_4$ to crystallize in the form of nanoparticles.

Said particles were coated with $TiO_2$ by using the titanium precursor $TiCl_4$. In fact, the reaction thereof with sodium hydroxide leads to the condensation of $TiO(OH)_2$ at the surface of $HfGeO_4$. A heat treatment at 500° C. for a duration comprised between 1.5 hours and 3 hours then allowed the conversion of $TiO_2$ to an anastase crystalline form, endowed with photocatalytic properties. Silica coating was carried out using TEOS. The slow and controlled hydrolysis of TEOS in alcohol and ammonia medium led to the formation of a layer of silica at the surface of the particles.

3. Biocompatibility of the Nanoparticles

The biocompatibility and the absence of in vitro toxicity of the silica-coated nanoparticles were tested in vitro on the cell lines MCF7, KB and UCI. The nanoparticles (30 to 1000 pg of particles/1000 cells) were incubated with said cells for 24, 48 and 72 hours. Cell survival was evaluated as follows:

$$Rsur = \frac{nombre\ de\ cellules\ vivante\ (avec\ particules)/}{nombre\ de\ cellules\ vivante\ (sans\ particules)/} \\ \frac{nombre\ de\ cellule\ mortes\ (avec\ particules)}{nombre\ de\ cellule\ mortes\ (sans\ particules)}$$

Figure 4:
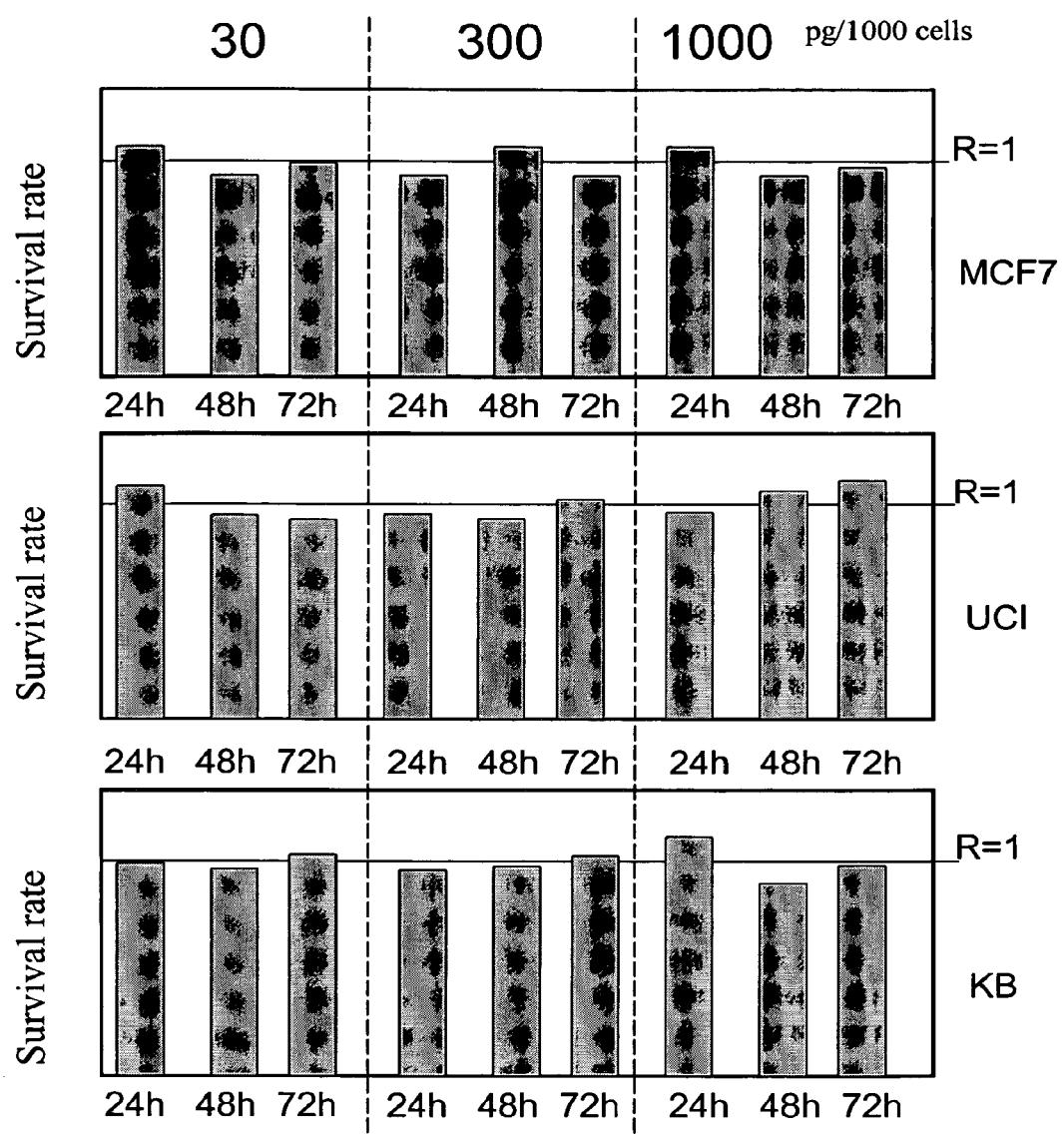
FIG. 4 shows cell survival rates after incubation with the nanoparticles.

Survival rate=no. of living cells (with particles)/no. of dead cells (with particles)/no. of living cells (without particle)/no. of dead cells (without particle) There was no significant difference in survival rates and cell division in comparison with the controls, as shown in FIG. 4.

4. Nanoparticle Targeting and Internalization

Figure 5:
FIG. 5 is a confocal laser scanning microscopic image showing the accumulation of nanoparticles (in gray on the slide) in the cell membranes.

The targeting and specific penetration of the particles (with surface targeting components) into the cells via surface receptors were observed by confocal laser scanning microscopy. The nanoparticles were coated with silica and functionalized with LHRH via a chemical bond (as described in Lévy et al., Chem. Mater. 2002, 14(9) pp 3715; Nanochemistry: *"Synthesis and Characterization of Multifunctional Nanoclinics for Biological Applications"*). The nanoparticles were incubated for 24 hours with MCF7 cells (carrying the LHRH receptor) and observed by confocal laser scanning microscopy. FIG. 5, which corresponds to an image recorded after 24 hours, reveals an accumulation of nanoparticles in the cell membranes and nuclei.

5. Protocol of Administration in Animals and Treatment

The nanoparticles were dispersed in isotonic solution (PBS, saline) at concentrations ranging from 1 to 20 mg/ml and injected in a volume of 0.5 ml by the intravenous, intratumoral or intraperitoneal route. 24 to 48 hours post-injection, the animals were exposed to X rays as follows:

Whole body for diagnosis or treatment of metastases. The X rays can be generated by standard radiographic equipment;

Focused for the treatment of a solid tumor or a specific body region.

Additional strategies can be employed:

a single injection followed by multiple X ray exposures;
multiple injections (several weeks apart), each followed by a single or multiple exposures;
multiple injections (several days apart), followed by a single or multiple exposures.

We claim:

1. A method for inducing the lysis or destruction of cancer cells, in vitro, ex vivo or in vivo, comprising (i) contacting cancer cells with one or more biocompatible composite particles or nanoparticle aggregates which can generate free radicals or heat when excited by X rays applied by using a system of radiotherapy or radiography, each of said biocompatible composite particle comprising
    a nucleus comprising a first inorganic compound that absorbs X rays and emits UV-visible energy, and said nucleus further comprising a second, inorganic or organic compound that absorbs said UV-visible energy and then produces said free radicals on contact with water or oxygen, said composite particle
    optionally additionally comprising a biocompatible coating allowing the diffusion of small molecules and free radicals,
    during a period of time sufficient to allow the particles or aggregates to penetrate inside the cancer cells and, (ii) exposing the cells to X rays, said exposure inducing the lysis or destruction of said cancer cells.

2. A method of cancer treatment, comprising (i) administering biocompatible composite particles or nanoparticle aggregates, which can generate free radicals or heat when excited by X rays applied by using a system of radiotherapy or radiography, to a patient suffering from a cancer, each of said biocompatible composite particle comprising:
    a nucleus comprising a first inorganic compound that absorbs X rays and emits UV-visible energy, and said nucleus further comprises a second, inorganic or organic compound, that absorbs said UV-visible energy and then produces said free radicals on contact with water or oxygen, said composite particle
    optionally additionally comprising a biocompatible coating allowing the diffusion of small molecules and free radicals,
    in conditions allowing the particles or nanoparticle aggregates to penetrate inside the cancer cells, and (ii) subsequently treating the patient in the presence of X rays, leading to an alteration, disturbance or functional destruction of the patient's cancer cells, thereby treating the cancer.

3. A method of cancer treatment, comprising (i) administering a composition comprising biocompatible composite particles or nanoparticle aggregates, which can generate free radicals or heat when excited by X rays applied by using a system of radiotherapy or radiography, to a patient suffering from a cancer, each of said biocompatible composite particle comprising:
    a nucleus comprising a first inorganic compound that absorbs X rays and emits UV-visible energy, and said nucleus further comprising a second, inorganic or organic compound, that absorbs said UV-visible energy and then produces said free radicals on contact with water or oxygen, said composite particle
    optionally additionally comprising a biocompatible coating allowing diffusion of small molecules and free radicals,
    in conditions allowing the particles or nanoparticle aggregates to penetrate inside the cancer cells, and (ii) subsequently treating the patient in the presence of X rays, leading to an alteration, disturbance or functional destruction of the patient's cancer cells, thereby treating the cancer.

* * * * *